(12) United States Patent
Boguszewski et al.

(10) Patent No.: US 10,638,722 B2
(45) Date of Patent: May 5, 2020

(54) ECOLOGICALLY RELEVANT SYSTEM AND A METHOD FOR TESTING SPONTANEOUS SOCIAL INTERACTIONS IN GROUP-HOUSED MICE

(71) Applicants: INSTYTUT BIOLOGII DOSWIADCZALNEJ IM. MARCELEGO NENCKIEGO PAN, Warsaw (PL); CENTRUM FIZYKI TEORETYCZNEJ PAN, Warsaw (PL)

(72) Inventors: Pawel Boguszewski, Warsaw (PL); Bartlomiej Juszczyk, Warsaw (PL); Grzegorz Kasprowicz, Chyliczki (PL); Ewelina Knapska, Pruszkow (PL); Rafal Krawczyk, Warsaw (PL); Szymon Leski, Pruszkow (PL); Alicja Puscian, Warsaw (PL); Pawel Rasinski, Jozefow (PL); Lech Mankiewicz, Warsaw (PL)

(73) Assignees: INSTYTUT BIOLOGII DOSWIADCZALNEJ IM. MARCELEGO NENCKIEGO PAN, Warsaw (PL); CENTRUM FIZYKI TEORETYCZNEJ PAN, Warsaw (PL)

( * ) Notice: Subject to any disclaimer, the term of this patent is extended or adjusted under 35 U.S.C. 154(b) by 236 days.

(21) Appl. No.: 15/763,110

(22) PCT Filed: Feb. 11, 2016

(86) PCT No.: PCT/EP2016/052914
§ 371 (c)(1),
(2) Date: Mar. 25, 2018

(87) PCT Pub. No.: WO2017/054933
PCT Pub. Date: Apr. 6, 2017

(65) Prior Publication Data
US 2018/0271052 A1 Sep. 27, 2018

(30) Foreign Application Priority Data

Sep. 30, 2015 (PL) .................................... 414188

(51) Int. Cl.
*A01K 1/03* (2006.01)
*A01K 29/00* (2006.01)
(Continued)

(52) U.S. Cl.
CPC ............ *A01K 1/031* (2013.01); *A01K 11/006* (2013.01); *A01K 29/005* (2013.01);
(Continued)

(58) Field of Classification Search
CPC .... A01K 1/031; A01K 29/005; A01K 11/006; A61B 5/1105
See application file for complete search history.

(56) References Cited

U.S. PATENT DOCUMENTS

| 4,574,734 A * | 3/1986 | Mandalaywala | ...... A01K 1/031 119/421 |
| 5,608,209 A * | 3/1997 | Matsuda | .............. A61B 5/1105 119/421 |

(Continued)

FOREIGN PATENT DOCUMENTS

WO    WO-0192850 A1 * 12/2001 ............ F41H 11/132

*Primary Examiner* — Magdalena Topolski
*Assistant Examiner* — Kevin M Dennis
(74) *Attorney, Agent, or Firm* — Mark M. Friedman

(57) ABSTRACT

A system for testing spontaneous social interactions of group-housed mice placed in an experimental apparatus. The system includes a plurality of compartments (101-104) bridged by corridors (105). At least one compartment (101-104) has a perforated partition wall (106,107) separating the compartment into a territory available for mice (106b, 107b) and a territory to be explored by olfaction (106a, 107a). In the territory available for mice (106b, 107b), above the partition wall (106, 107), there is an infrared laser curtain (Continued)

(201). The system also includes a photographic device (202) for acquiring the intersection of a mouse in the light of the infrared curtain. In the territory to be explored by olfaction (106a, 107a), there is a source of olfactory stimuli (203).

12 Claims, 4 Drawing Sheets

(51) Int. Cl.
  *G06K 9/20* (2006.01)
  *G06K 9/00* (2006.01)
  *A01K 11/00* (2006.01)
  *A61B 5/11* (2006.01)

(52) U.S. Cl.
  CPC ........ *A61B 5/1105* (2013.01); *G06K 9/00335* (2013.01); *G06K 9/2036* (2013.01)

(56) References Cited

U.S. PATENT DOCUMENTS

| | | | |
|---|---|---|---|
| 5,717,202 A * | 2/1998 | Matsuda | A01K 1/031 119/421 |
| 6,637,372 B2 * | 10/2003 | Mauderli | A61B 5/4824 119/417 |
| 9,986,716 B1 * | 6/2018 | Betts-Lacroix | A01K 1/031 |
| 10,089,435 B1 * | 10/2018 | Betts-Lacroix | A61B 8/46 |
| 10,292,369 B1 * | 5/2019 | Heath | A01K 29/005 |
| 2003/0004652 A1 * | 1/2003 | Brunner | A01K 1/031 702/19 |
| 2005/0066910 A1 * | 3/2005 | Tecott | A01K 1/031 119/421 |
| 2007/0028918 A1 * | 2/2007 | Tsuyuki | A01K 1/031 128/203.12 |
| 2010/0111359 A1 * | 5/2010 | Bai | G06K 9/00335 382/103 |
| 2010/0175629 A1 * | 7/2010 | Garmon | A01K 1/02 119/419 |
| 2012/0180731 A1 * | 7/2012 | Garner | A01K 1/031 119/417 |
| 2014/0055248 A1 * | 2/2014 | Hammelbacher | A01K 1/031 340/10.6 |
| 2014/0167958 A1 * | 6/2014 | Kimchi | A01K 1/031 340/539.13 |
| 2014/0196666 A1 * | 7/2014 | Kuzniar | A01K 1/0107 119/479 |
| 2014/0251228 A1 * | 9/2014 | Jensen-Jarolim | A01K 29/005 119/421 |
| 2016/0270364 A1 * | 9/2016 | Woolf | A61B 5/1105 |
| 2016/0363692 A1 * | 12/2016 | Arpin | A01K 29/00 |
| 2017/0308755 A1 * | 10/2017 | Ala-Laurila | G06T 7/74 |
| 2018/0206447 A1 * | 7/2018 | Maurice | A61B 5/4088 |
| 2018/0279921 A1 * | 10/2018 | Datta | A61B 5/00 |

\* cited by examiner

ECOLOGICALLY RELEVANT SYSTEM AND A METHOD FOR TESTING SPONTANEOUS SOCIAL INTERACTIONS IN GROUP-HOUSED MICE

TECHNICAL FIELD

The present invention relates to a system and method for testing spontaneous social interactions in group-housed mice.

BACKGROUND

Animal models of social functioning disorders are commonly used in behavioural and biomedical research, aiming at developing new therapeutic and pharmacologic solutions. There is a whole range of behavioural assays for evaluation of the conspecific-related behaviour in mice. Nevertheless, available behavioural tasks usually do not allow for the longitudinal observation of between-littermate interactions. Moreover, the 'conventional' tasks are carried out on socially isolated animals and require animal handling by an experimenter, both of which are highly stressful for rodents.

These aforementioned factors may exert confounding anxiety-related effects on obtained data, as well as cause significant between-laboratory differences. Therefore, there is a strong need to standardize behavioural measures relevant to murine social behaviours using a fully automated system, which imitates features of the ecological niche of small rodents.

Ecologically relevant, automated tests for the assessment of mouse cognitive functioning are well established and often employed for the evaluation of mouse models of intellectual impairment, as well as in research that aims to characterize behavioural patterns in different strains of laboratory mice.

However, there are still no reliable and, at the same time, ecologically pertinent assays of social behaviour, that may be conducted for longer periods of time in group-housed mice and being fully automated.

Therefore, there is a need for assays, fulfilling the above-mentioned criteria, simultaneously providing highly replicable results and the functional reliability of the analyzed behaviours. The development of the presented research technique would be highly valuable, because it allows for the reliable assessment of spontaneous conspecific-related interactions, and obtaining data on the character of these relations. The present invention provides such a technique. It also facilitates the dependable evaluation of experimental therapies and medical substances being tested in mouse models of social functioning disorders.

SUMMARY

The subject of the present invention is a system for testing spontaneous social interactions of group-housed mice placed in an experimental apparatus comprising a plurality of compartments bridged by corridors. At least one compartment has a perforated partition wall separating the compartment into a territory available for mice and a territory to be explored by olfaction. In the territory available for the mice and above the partition wall, there is an infrared laser curtain, wherein the system comprises a photographic device for acquiring the intersection of a mouse in the light of the infrared curtain. In the territory to be explored by olfaction there is a source of olfactory stimuli.

Preferably, the system comprises at least one wireless electronic tag having an identification number and a transceiver device injected into a mouse, for determining the localization of animals in the system, wherein the wireless electronic tag communicates with a computer.

Preferably, the wireless electronic tag comprises a system for measuring the orientation of the body of the mouse and a system for measuring the rotation of the mouse.

Preferably, the wireless electronic tag comprises a 6-axis accelerometer and/or a 3-axis magnetometer.

Preferably, the wireless electronic tag comprises a system for monitoring physiological parameters of animal's body.

Preferably, the wireless electronic tag comprises systems for monitoring the temperature and/or activity of animal's brain.

Preferably, the wireless tag comprises an array of three low-frequency antennas connected to a receiver for decoding the identifiers of the transceiver device and for activating the remaining elements of the injectable wireless tag (i.e. through injection).

Preferably, the wireless tag comprises three low-frequency antennas oriented to receive signals and/or to measure the intensity of signals with respect to three mutually perpendicular axes (X, Y, Z).

Preferably, at least one of the three antennas is connected to the wireless tag battery by means of an embedded charger.

Preferably, the compartment with the partition wall comprises an infrared display located in the field of view of the photographic device, displaying an actual time and/or an identification number or a mouse present in proximity of the partition wall.

The object of the invention is also a method of testing spontaneous social interactions among group-housed mice placed in an experimental apparatus comprising a plurality of compartments bridged by corridors. The method comprises the following steps:

placing, in at least one compartment, a perforated partition wall to separate the compartment into a territory available for mice and a territory to be explored by olfaction;

providing, in the territory to be explored by olfaction, a source of olfactory stimuli;

providing, in the territory available for mice above the partition wall, an infrared laser curtain and acquiring, by means of a photographic device, an intersection of a mouse in the light of the infrared curtain.

Preferably, the method also comprises injecting the mice with wireless electronic tags with an identification number and a transceiver device for transmitting the signals from monitoring systems of the animal and registering the signals from monitoring systems of the animal.

The present invention addresses the problems of anxiety related factors that may interfere with reliable results dealing with rodent behaviours. It comprises standardized, adequate experimental protocols and proves that ecologically relevant social behaviours can be measured under the laboratory conditions. Moreover, the presented solution enables a significant reduction of time and manpower routinely needed to perform behavioural studies. The present invention allows for the reliable assessment of social interactions and gathering knowledge on functional relations within group-housed mice. The proposed assay is also likely to contribute to the testing of possible therapeutic approaches with the use of mouse models of human social impairment.

BRIEF DESCRIPTION OF FIGURES

These and other subjects of the present invention, are accomplished by testing spontaneous social interactions in group-housed mice. Further details and features of the present invention, its nature and various advantages will become more apparent from the following detailed description of the preferred embodiments shown in a drawing, in which.

DETAILED DESCRIPTION

Figure 1:
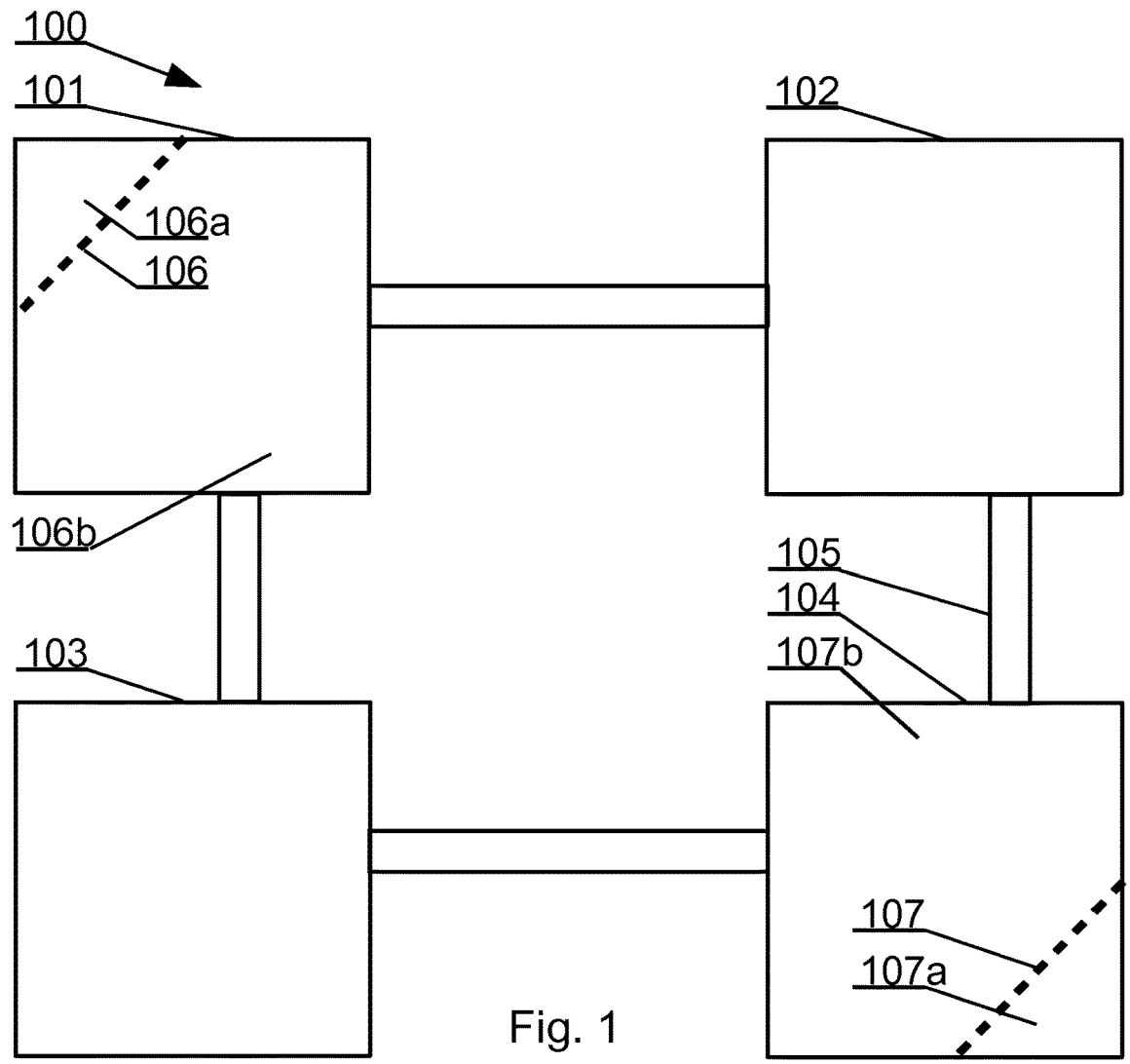
FIG. 1 represents a diagram of the housing system according to the present invention.

In a natural habitat, mice spent their time mostly being away from open space and, as nocturnal animals, being active mostly at night. These factors are often underestimated by researchers assessing biomedical research on animal models, where behaviour and cognitive functioning of rodents is used. Moreover, assumptions made about the behavioural functioning of rodents based on phenomena observed in one-trial tests may mislead the interpretation of the results.

Nocturnal activity and a tendency to stay hidden should not be neglected, when making presumptions about social interactions and investigating conspecific-related behaviours in mice.

The present invention aims to create a behavioural test reflecting these key features of rodents' natural habits and environment, as well as provide subjects the possibility to spread out within a demarked territory (experimental environment). The latter seems to be highly meaningful, as in the wild populations small rodents may travel as far as 1000 meters within their habitat.

Accordingly, the mice are provided with shadowed areas and narrow tunnels (corridors), which imitate semi-natural burrows. Investigation of small rodent behaviour in their natural habitat shows that artificial, narrow, tube-shaped corridors providing shelter from predators, placed under the ground level by researchers, are readily used by mice as commotion tracks.

It is typical for the small rodents to live in numerous and family-based groups. This fact determines the central role of social interactions in mouse survival and reproductive success. It was established that, when possible, unfamiliar rodents tend to avoid each other. If forced to interact openly, they often become aggressive. Moreover, rodents follow social scents and are especially prone to explore odours of previously met or closely genetically related individuals, than unknown or distinctly genetically related ones.

Interestingly, mice form social relations faster and become familiar more rapidly with conspecifics with a social scent they had encountered before. These observations point to the key reflection, that smell is a dominating sense in rodents and it decides about survival of a group or species. Taking this fact into consideration, it is crucial to perform dependable and accurate analyses of social behaviour of these animals.

Olfaction is absolutely essential to mouse survival from the postnatal day 1. It is known that pups can find the nipple of their mother based on olfactory cues. It has also been proven that, for mice of both sexes, odour perception and scent based communication play a key role in all important social behaviours: mating and reproduction, territory maintenance and developing a stable inter-group hierarchy. Odour-based communication is also considered to be of high priority in integration of mice populations in the wild. For example, BTBR male mice, considered an extensive face validity model of autism spectrum disorders, display reduced scent marking behaviour, which is consistent with the results of many well-replicated tests showing social deficits in this inbred strain.

For these reasons the system according to the present invention not only allows one to observe and analyze social interactions among subjects within an experimental group, but also represents animals with different types of social scents.

As previously described, in a natural habitat, even though mice avoid open interactions, they are prone to explore and investigate odours of social provenience. Based on this knowledge we aimed at assessing exploration related to social scent as the most natural type of social approach observed in mice.

FIG. 1 represents a diagram of the housing system according to the present invention. In this exemplary embodiment of the invention, it is a system of 4 housing cages, otherwise called compartments (101-104). However, it will be evident to the skilled person that more or fewer cages may be used in such a system. Utilized housing compartments may be deployed on multiple levels and connected by any number of intra-territorial corridors. It is also possible to implement changes in the shapes and sizes of the cages as required by particular experimental procedures.

The system allows for continuous data collection, animal housing and testing over a period of months. Except for scheduled, technical breaks and cleaning operations, such a system enables researchers to monitor and control an experiment remotely, from a PC located outside the testing room, thus not interfering with the experimental environment.

The housing compartments are bridged by a suitable number of tube-shaped corridors (105). These inter-territorial connections enable mice to freely travel between compartments and spend time with their preferred conspecific subgroup or favoured territory areas. The cages (101-104) may have a shape of a cube with a wall length of about 25 cm, and the corridors (105) may be about 30 cm long.

In order to individually identify animals in the system, all mice (or tested animals) are subcutaneously injected with a wireless tag (WT) under isoflurane anesthesia. Individual location of the electronically tagged mice is continuously recognized by the system with a high positioning resolution (e.g. down to a one centimeter) range. The wireless tag is equipped with an inductive power transfer antenna and an ISM bandwidth transceiver that transmits a unique ID number and animal parameters such as body temperature, its position in a three-dimensional space and brain activity. Under the cage, an array of antennas is installed that are used for both energy transfer and localization purposes.

The assay is controlled via a computer. This solution allows full automation of the assay, continuous data acquisition and minimization of impact of human handling on animal behaviour.

In two out of the four housing compartments there is a perforated partition wall (106, 107) that physically separates a small part (106a, 106b) of the territory, where stimuli (203) (e.g. olfactory cues of social or non-social provenience) might be presented to the subjects. The mice are free to move in the part (106b, 107b) and cannot enter the part 106a, 107a. Among olfactory cues of social provenience, that may be presented behind the perforated partition wall, the most applicable are: fresh urine of male/female/juvenile mice of the same/different strain and age, bedding freshly obtained from the housing cage/cages of male/female/juvenile mice of the same/different strain and age, scent marks of male/female/juvenile mice of the same/different strain and age gathered during new territory exploration procedures, toys or other objects that were kept in the housing compartment of male/female/juvenile mice of the same/different strain and age. Non-social olfactory stimuli that may be used for control purposes should be adjusted to the type and character of a source of the social scent e.g. fresh bedding, clean toys and other equipment used for housing enrichment purposes, saline. A part of the territory intended for the placement of the olfactory stimuli is substantially air-tight, thus allowing for long-lasting scent preservation. It is also important to keep the stimuli from diffusing before the moment of their manual or automated placement in the proper part of the apparatus.

The system may additionally be equipped with an optoelectronic detection system allowing for an individualized assessment of sniffing behaviour in response to olfactory stimuli. The detection system, as well as a preferred installation, has been shown in FIG. 2.

A laser curtain (201) consists of two or more commercially available line laser generators. They generate a plane of light, about 1 mm thick and of the width (angle) allowing for covering the area where animals investigate the olfactory stimuli. When animal is crossing the plane of light, an infrared photographic device (202) (a camera or a video camera), which is situated perpendicularly to the curtain, acquires its intersection. It is crucial to locate the curtain 1-2 mm from the perforated partition wall, for the curtain to illuminate an animal, which is leaning on the partition wall or smelling it from many sides. Two or more sources of light are required to provide detection quality.

An image acquired by the photographic device consists of the contours of animals' paws, noses, tails or fur and is identified by an algorithm working on the computer in real time. The algorithm's work is synchronized with the time of the positioning system and the readout of the subcutaneous electronic tags, by the means of an LED display working in the infra-red spectrum, which is placed in the field of photographic device's view, at its very edge. The display may consist of 32 IR LEDs that may show a millisecond number from the position measurement system. The number may be encrypted in Grey's code and updated for example every 10 milliseconds, throughout wireless position measurement and data acquisition system. The algorithm working on the connected computer may recognize a sequence of LED lighting and extinguishing and thus decode the time of the measurement. The described time assessment is immensely important, as it enables the correlation of data acquired by the laser curtain with data obtained by the position measurement system, which further makes it possible to ascertain which animal touched the partition wall at a given time point and its physical localization. The delay introduced by the image processing chain on the computer and photographic devices themselves is too great to assess which animal is present in the acquired image without any additional synchronization system.

The system of position measurement and data readout from the electronic tag injected into the animal's body may also send data about the current position of the animal and the precise local time to the abovementioned computer. Thanks to this process, the algorithm is able to correlate both measurements and assess, which animal was leaning on or touching the perforated partition wall in a given time point.

Photographic devices of the required characteristics present on the market are mostly based on CMOS technology. However, it is also possible to utilize any other photographic device possessing sensitivity in the near infra-red spectrum, such as CCD cameras. Regardless of the employed photographic device type, it is optimal to use one equipped with a global shutter.

Thus, the laser curtain function is as follows: once an animal approaches the perforated partition wall (106, 107), it is illuminated from the sides by the laser curtain, and simultaneously a photographic device (202) captures its cross-section. The dedicated, real time image processing algorithm discriminates the animal body part that touched the partition wall, allowing for distinguishing actual sniffing from any other behavioural performance. Such object recognition, behaviour recognition and image analysis methods will be readily known to a person skilled in the art of objects detection.

Figure 2:
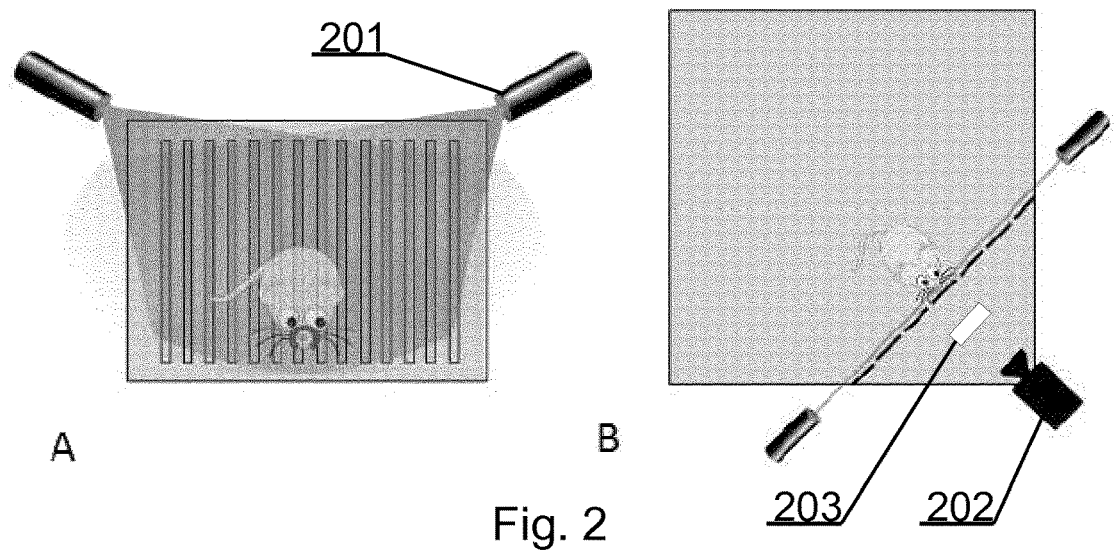
FIG. 2 represents a diagram of a laser-employing visual sniffing detection system.

Element A in FIG. 2 represents a front view, while element B in FIG. 2 represents a top view of the described system.

As previously described, the operation of the optoelectronic detection system is synchronized with the localization system using, for example an infrared LED display, in the photographic device's field of view, so that every sniffing behaviour is correlated with the time and ID of the particular subject.

Figure 3:
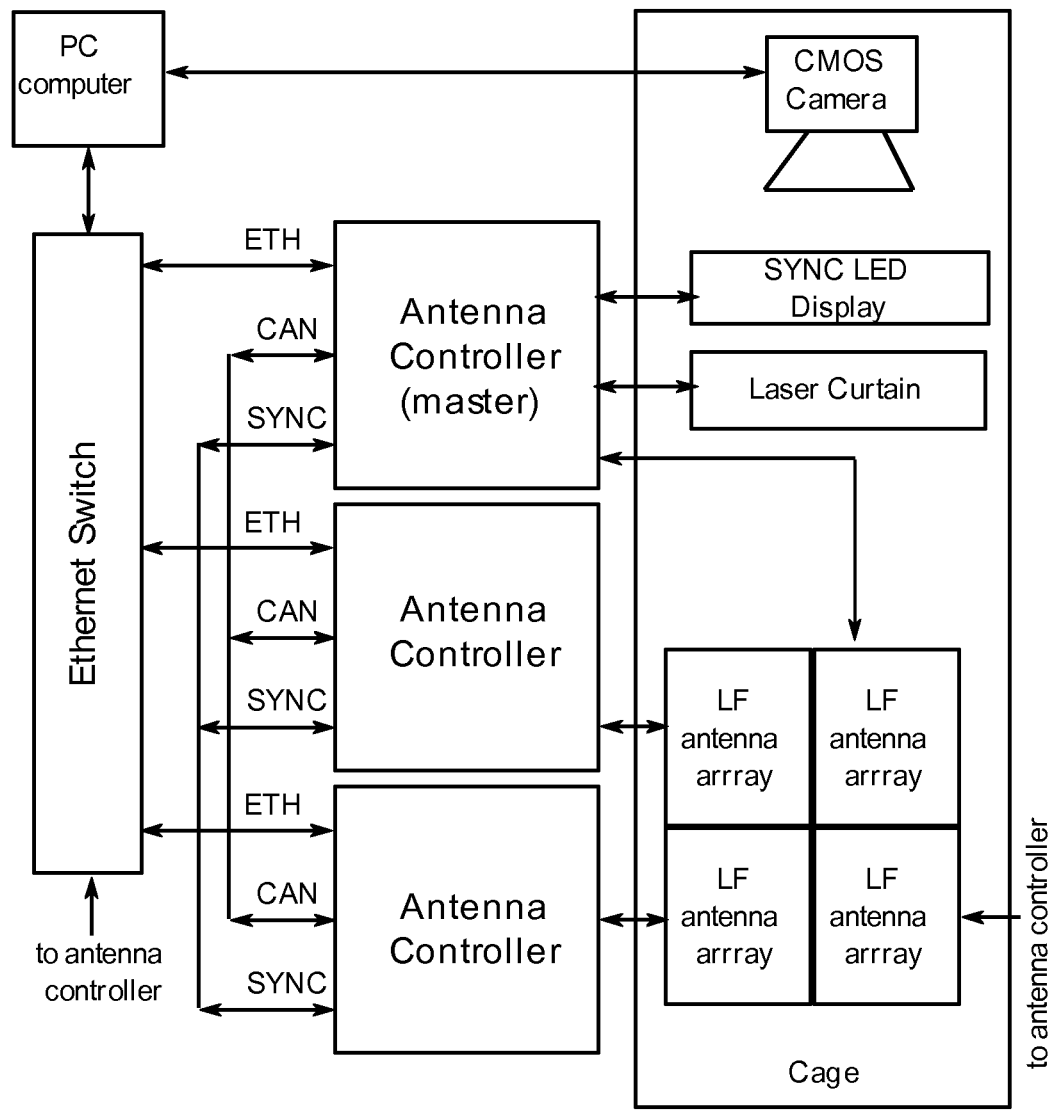
FIG. 3 represents a schematic of the electronic cage control system.

The cage control system comprises a general-purpose computer (such as a PC) and several peripheral blocks as shown in FIG. 3. The system further comprises a master antenna controller that controls the laser curtain, an IR LED display, and a Low Frequency (LF) coil array. The master antenna controller serves as time master for other modules.

Additionally, the system comprises several secondary antenna controllers with LF coil arrays and a synchronizing IR LED display, wherein the display is used in to synchronize the optoelectronic detection system with the positioning system.

Finally, the system may be equipped with a communication means, such as an Ethernet Switch, used in order to connect all antenna controllers with the general-purpose computer.

Figure 4:
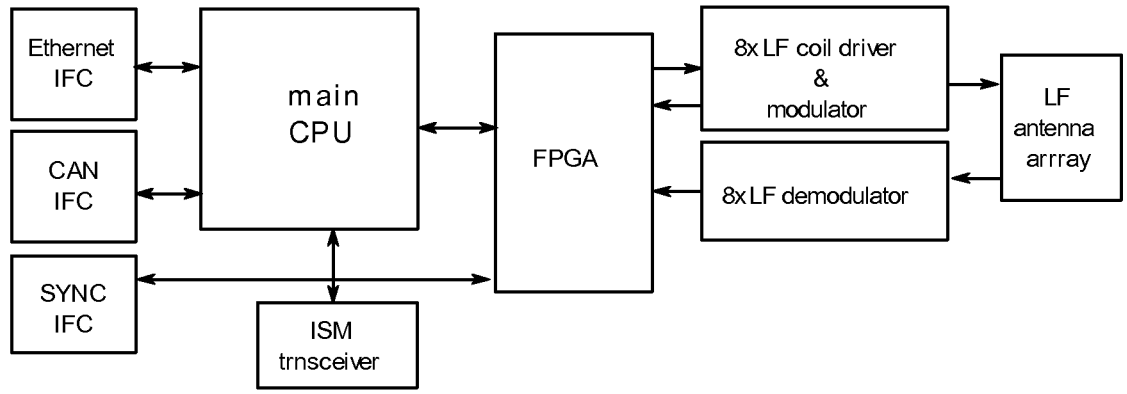
FIG. 4 represents a schematic of the LF Antenna array controller.

The antenna controller, as shown in FIG. 4, is a main building block of the cage control system. It performs several functions: ISM (Industrial, Scientific and Medical band) transceiver—uses low power protocol to communicate with WT, Eight Low Frequency (LF) power transmitters used to provide power to charge accumulator in the WT, finally eight LF modulators—used to wake-up the microprocessor on WT board and transfer unique ID of the coil. This ID is used to estimate localization of WT in reference to the LF coil number.

The Eight LF demodulators are used in order to detect the presence of the WT over the LF coil.

The antenna controller may communicate over Ethernet with the control PC and may be equipped with a CAN interface, used in order to provide fast communication channel between antenna controllers.

A synchronization (SYNC) interface is used to provide common time reference while FPGA (Field Programmable Gate Array), circuits and/or a CPU are used to provide complex vector steering of the LF array, synchronization and communication with the general purpose computer (PC).

In order to increase positioning accuracy, each wireless tag is preferably equipped with a 6-axis accelerometer and a 3-axis magnetometer. The accelerometer measures an animal's body orientation with reference to gravity, while the magnetometer estimates animal rotation inside the cage. Such a set of data precisely describes the momentary position and orientation of the animal's body inside the cage and enables the advanced study of interactions between animals, i.e. detection of social behaviours.

Absolute animal position estimation is determined using an array of Low Frequency (LF) coils embedded in the cage's bottom. The coils are selectively controlled by driver circuits. They are enabled in a special sequence so as not to disturb the neighboring coils. Each coil transfers a unique ID pattern that is detected using the tag reception antennas included in the electronic tags. Then, the wireless electronic tag transmits the matched coil ID, its own ID, magnetometer and accelerometer sensor data and physiological data using the embedded ISM transmitter.

Figure 5:
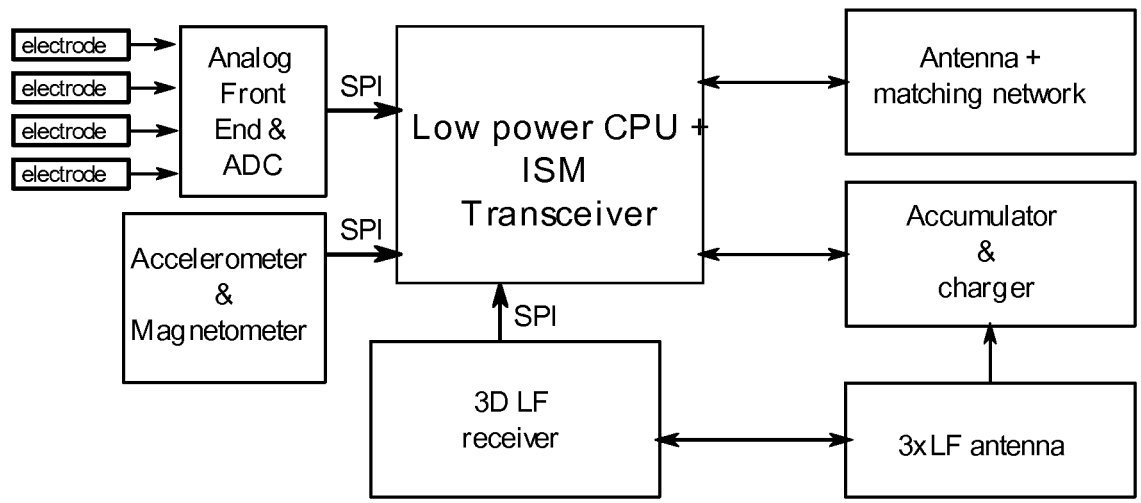
FIG. 5 represents a Wireless Tag block schematic.

In order to prolong battery operation and improve tag reaction time, the LF field is also used to wake-up the embedded WT microcontroller and sensors. The LF field is also used to charge a miniature battery, preferably present in the wireless tag WT. The coil driver regulates power accordingly to the function performed: wakeup, positioning or energy transfer. FIG. 5 presents schematic of the LF Antenna array controller.

FIG. 5 presents the injectable tag (WT) schematic. An array of 3 LF antennas are connected to the LF micro power receiver, which decodes transmitter antenna IDs and also wakes up the tag processor from ultra-low power mode. Each tag has three LF antennas oriented to acquire X, Y and Z axis LF field magnitudes. One of the antennas is also used for power transfer. This charges the accumulator using an embedded charger Integrated Circuit (IC). All the tag resources are controlled by a low power CPU, which receives data from sensors and transmits them via embedded ISM transceiver.

Figure 6:
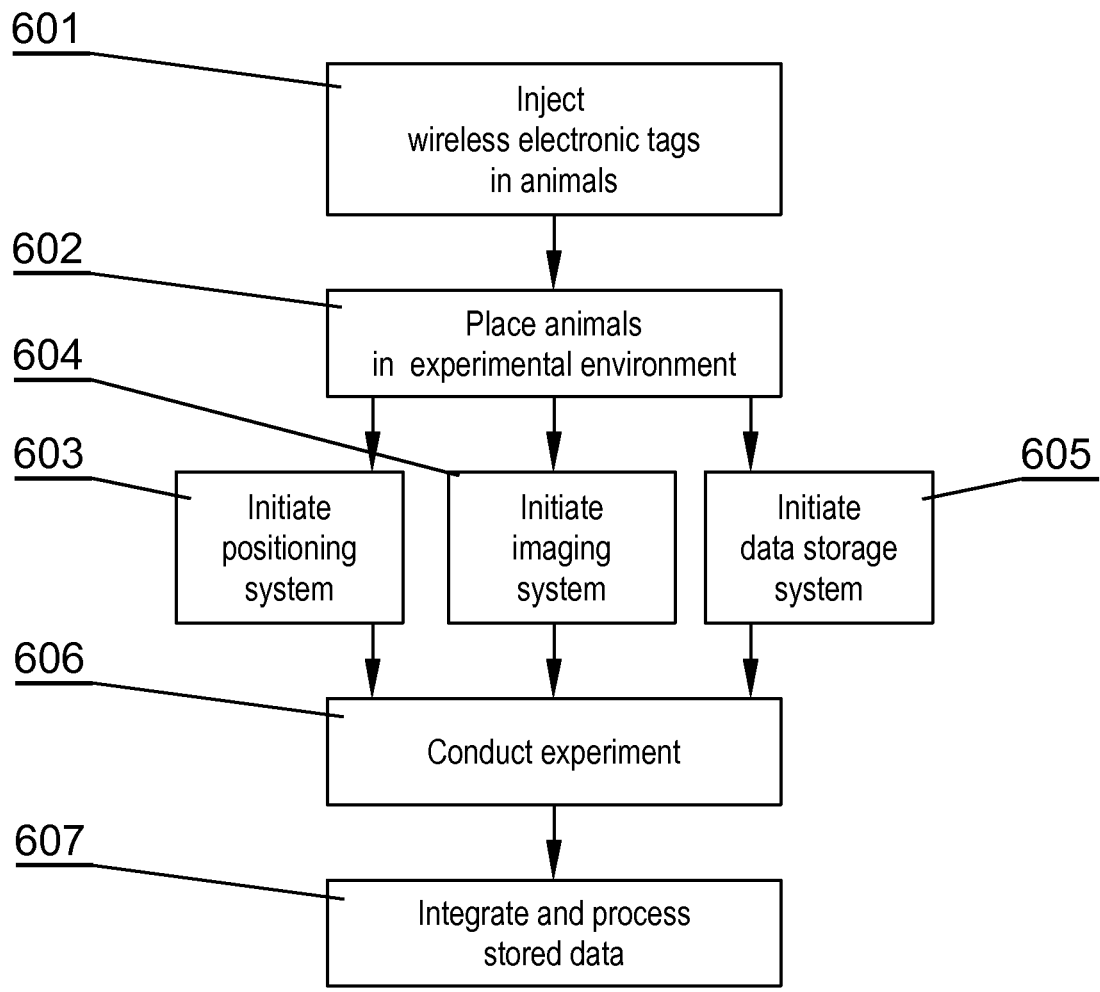
FIG. 6 represents a schematic of operation of the system.

FIG. 6 represents a general schematic of the operation of the system. Prior to the start of experimental procedures, in step 601, all subjects are subcutaneously injected with wireless tags and adapted to living in a particular social group of mice. Next, in step 602, group-housed animals are placed in the system and adapt to its specific environment for a certain period of time, depending on the subsequent experimental procedures. During this period and later, throughout the experiment after olfactory stimuli presentation, the animals are continuously tracked by the positioning system, which is initiated in step 603. As it is important to establish the native behavioural preferences and patterns of the mice, the exploration of the perforated partition wall is also continuously assessed by a system comprising the laser curtain integrated with the imaging system (for example, a suitable camera and LED display), which is initiated in step 604. All assessed the; parameters are stored at the operating computers in real-time. Hence, data about animals' position, physiological parameters, orientation with reference to gravity and rotation inside the cage, as well as information of exploration of the perforated partition wall, are constantly collected and stored by the customized software, initiated in step 605. It is to be expected, that olfactory stimuli display may lead to enhanced locomotor activity of the subjects, as well as intensified exploration and spending a considerable amount of time near the perforated partition walls. However, olfactory stimuli presentation does not affect the operation of the electronic systems. At that point, all implemented solutions are already continuously collecting animal behavioural data, allowing for testing their performance throughout the adaptation period and later on, following experimental scent presentation. The continuous data collection does not stop until the experiment is ended at the end of step 606.

Further, data from all systems are integrated and processed in step 607, which finally leads to obtaining an individualized assessment of social interactions and social/non-social olfactory stimuli exploration for each of the group-housed subjects.

The invention claimed is:

1. A system for testing spontaneous social interactions of group-housed mice placed in an experimental apparatus the system comprising:
   a plurality of compartments bridged by corridors,
   wherein at least one compartment of the plurality of compartments comprises a perforated partition wall that separates said at least one compartment into a territory available for mice and a territory to be explored by olfaction,
   an infrared laser curtain in the territory available for mice, above the perforated partition wall,
   a photographic device configured to acquire an intersection of a mouse in a light of the infrared laser curtain; and
   a source of olfactory stimuli the territory to be explored by olfaction.

2. The system according to claim 1, further comprising at least one wireless electronic tag having an identification number and a transceiver device, the wireless electronic tag configured to be injected into a mouse, for determining localization of the mouse in the system, wherein the wireless electronic tag communicates with a computer.

3. The system according to claim 2, wherein the wireless electronic tag comprises a system for measuring an orientation of a mouse's body and a system for measuring a rotation of the mouse body.

4. The system according to claim 3, wherein the wireless electronic tag comprises at least one of: a 6-axis accelerometer and a 3-axis magnetometer.

5. The system according to claim 4, wherein the wireless electronic tag comprises a system for monitoring physiological parameters of the mouse body.

6. The system according to claim 5, wherein the wireless electronic tag comprises at least one of: a system for monitoring a temperature and a system for monitoring an activity of a mouse brain.

7. The system according to claim 6, wherein the wireless electronic tag comprises an array of three low-frequency antennas connected to a receiver for decoding identifiers of the transceiver device and for activating remaining elements of the wireless electronic tag.

8. The system according to claim 7, wherein the wireless electronic tag comprises the three low-frequency antennas are oriented to at least one of: receive signals and measure the intensity of signals with respect to three axes (X, Y, Z) perpendicular to one another.

9. The system according to claim 8, wherein at least one of the three antennas is connected to a battery of the wireless electronic tag by means of an embedded charger.

10. The system according to claim 1, wherein at least one compartment of the plurality of compartments comprises the partition wall comprising an infrared display located in a field of view of the photographic device, that displays at least one of: an actual time and an identification number or the mouse present in the proximity of said partition wall.

11. A method for testing spontaneous social interactions of group-housed mice placed in an experimental apparatus, the experimental apparatus comprising a plurality of compartments bridged by corridors, the method comprising the following steps:

placing, in at least one compartment of the plurality of compartments, a perforated partition wall to separate said at least one compartments into a territory available for mice and a territory to be explored by olfaction;

providing, in the territory to be explored by olfaction, a source of olfactory stimuli;

providing, in the territory available for mice above the perforated partition wall, an infrared laser curtain, and acquiring, by means of a photographic device, an intersection of a mouse in a light of the infrared curtain.

12. The method according to claim 11, further comprising providing each mouse with a wireless electronic tag having an identification number and a transceiver device for transmitting signals from monitoring systems of the mouse and registering the signals from the monitoring systems of the mouse.

* * * * *